United States Patent [19]
Hook et al.

[11] Patent Number: 5,648,240
[45] Date of Patent: Jul. 15, 1997

[54] **MHC II ANALOG FROM *STAPHYLOCOCCUS AUREUS***

[75] Inventors: Magnus Hook, Houston, Tex.; Klas Jonsson, Kalmar, Sweden; Joseph M. Patti, Missouri; Sivashankarappa Gurusiddappa, Houston, both of Tex.

[73] Assignee: Texas A&M University, College Station, Tex.

[21] Appl. No.: 248,021

[22] Filed: May 24, 1994

[51] Int. Cl.$^6$ .................. C12N 15/31; C07K 14/31; A61K 39/085
[52] U.S. Cl. ............... 435/69.3; 435/252.3; 435/320.1; 424/185.1; 424/243.1; 530/300; 530/350; 530/825; 536/23.7
[58] Field of Search .................. 536/23.7; 424/184.1, 424/185.1, 190.1, 243.1; 514/44; 530/350, 395, 868; 435/69.3

[56] References Cited

U.S. PATENT DOCUMENTS

| | | |
|---|---|---|
| 4,425,330 | 1/1984 | Norcross ................................. 424/92 |
| 4,795,803 | 1/1989 | Lindberg ................................. 530/324 |
| 5,034,515 | 7/1991 | Proctor ................................. 536/1.1 |
| 5,198,215 | 3/1993 | De Cueninck ................................. 424/92 |

FOREIGN PATENT DOCUMENTS

| | | | |
|---|---|---|---|
| 20294349 | 12/1988 | European Pat. Off. | ........ C12N 15/00 |
| 10343137 | 11/1989 | European Pat. Off. | ........ C12N 15/00 |
| 20342173 | 11/1989 | European Pat. Off. | ........ C12N 15/00 |
| WO85/05037 | 11/1985 | WIPO | ........ A61K 39/00 |
| WO92/02555 | 2/1992 | WIPO | ........ C07K 15/04 |
| WO92/07002 | 4/1992 | WIPO | ........ C07K 15/04 |
| WO94/06830 | 3/1994 | WIPO | ........ C07K 15/04 |

OTHER PUBLICATIONS

Abou–Zeid, Infection and Immunity, 59:2712–2718, 1991.
Arroyo, Molecular Microbiology, 6:853–862, 1992.
Beachey, The Journal of Infectious Diseases, 143:325, 1981.
Becker, Cardiovascular Research, 21:813, 1987.
Bremwell, Infection and Immunity, 59:2615, 1991.
Buxton, Microbial Pathogenesis, 8:441–448, 1990.
Caparon, Infection and Immunity, 59:1811–1817, 1991.
Chhatival, Infect. Immun., 55:1878–1883, 1987.
Chhatwall, Infection and Immunity, 58:3015–3019, 1990.
Chin & Marx, Science, Apr. 15, 1994.
Ciborowski, J. Med. Microbiol., 37:376–381, 1992.
Esperson, Infection and Immunity, 37:526–531, 1982.
Finlay, Current Biology, 2:815–820, 1990.
Flock, The EMBO Journal, 6:2351–2357, 1987.
Foster, Vaccine, 9:221–227, 1991.
Froman, The Journal of Biological Chemistry, 262:6564–6571, 1987.
Haapasalo, Infection and Immunity, 60:2058–2065, 1992.
Hanahan, J. Mol. Biol., 166:557–580, 1983.
Hanski, Proc. Natl. Acad. Sci., 89:6172–6176, 1992.
Hanski, Infection and Immunity, 60:5119–5125, 1992.
Harrowe, J. Clin. Invest., 85:1324–1327, 1990.
Hasty, Infection and Immunity, 60:2147–2152, 1992.
Holderbaum, Infection and Immunity, 54:359–364, 1986.
Holderbaum, Collagen Rel. Res., 5:261–271, 1985.
Homonylo–McGavin et al., Infect. Immunol., 61:2479–2485, 1993.
Joh, Biochemistry, 33:6086–6092, 1994.
Kuusela et al., Nature, 276:718–720, 1978.
Kuypers, Infection and Immunity, 57:2306–2312, 1989.
Laemnli, Nature, 227:680–685, 1970.
Lopes et al., Science, 229:275–277, 1985.
Lowrance, The Journal of clinical Investigation, 86:7–13, 1990.
Mamo, Vaccination against Staphylococcus ... , Jul. 1993.
Marmur, J. Mol. Biol., 3:208–218, 1961.
McGavin, The Journal of Biological Chemistry, 266:8343–8347, 1991.
McGavin, The Journal of Biological Chemistry, 268:23946–23953, 1993.
McGavin, Infection and Immunity, 61:2479–2485, 1993.
Morrison & Bayse, Biochemistry, 9:2995–3000, 1970.
Nelson, Flem. Vet. J., 62:111–125, 19.
Patti, Biochemistry, 32:11428–11435, 1993.
Patti, Infect. Immunity, 62:152–161, 1994.
Proctor, Reviews of Infec. Diseases, 9:335–340, 1987.
Raja, Infection and Immunity, 58:2593–2598, 1990.
Rosalska, Scand, J. Immunol., 37:575–580, 1993.
Ryden, Eur. J. Biochem., 184:331–336, 1989.
Ryden, The Journal of Biological Chemistry, 258:3396–3401, 1983.
Sanger, PNAS, 74:5463–5467, 1977.
Sansonetti, Med. Microbiol. Immunol., 182:223–232, 1993.
Schennings, Microbial Pathogenesis, 15:227–236, 1993.
Signas, Proc. Natl. Acad. Sci., 86:699–703, 1989.
Svanborg–Eden, Scan. J. Infect. Dis., 33:72–78, 1982.
Talay, Infection and Immunity, 60:3837–3844, 1992.
Towbin, PNAS, 76:4350–54, 1979.
Turnidge, Drugs, 45:353–366, 1993.
Wadstrom, The Staphylococci, pp. 37–52, 1991.
Westerlund, Molecular Microbiology, 9:687–694, 1993.
Braude, A. I. et al. (eds), *Infectious Disease and Medical Microbilogy*, pp. 236–242, W.B. Saunders Co., 1986.
Projan, S. et al., Nuc. Acids Res. 17:3305 (1989), "Nucleotide sequence of the beta–hemolysin gene of *Staphylococcus aureus*".

(List continued on next page.)

*Primary Examiner*—Thomas M. Cunningham
*Attorney, Agent, or Firm*—Arnold, White & Durkee

[57] ABSTRACT

*Staphylococcus aureus* can bind a number of different extracellular matrix proteins. Recent studies have shown that one particular Staphylococcus protein has the capacity of binding several different matrix proteins. The gene encoding this staphylococcal protein has been cloned and sequenced and the nucleic acid and amino acid sequences are provided as a feature of the present invention. This staphylococcal protein has a high degree of homology with eukaryotic MHC Class II antigens. Further analyses of the binding specificities of this protein reveal that it functionally resembles an MHC II antigen in that it binds synthetic peptides. Additionally, the present invention provides a vaccine and an in vivo vaccine against staphylococcal infections, and methods for using same.

23 Claims, 15 Drawing Sheets

OTHER PUBLICATIONS

Jonsson, K. et al., J. B. C. 270:2145–21460, "*Staphylococcus aureus* expresses a major histocompatibility complex class II analog". Sep. 15, 1995.

The QIAexpressionist, 2nd edition, Summer 1992, pp. 7–23. Published by QIAGEN, INC. Chatsworth, CA. 1992.

Weir, D. M. (ed), Handbook of Experimental Immunology, 2nd edition, Chapter 17, pp. 17.1–17.8, "Radioimmunoassay" by W. M. Hunter. Blackwell Scientific Publications, Oxford. 1973.

```
              10         20         30         40         50
              *          *          *          *          *
        AAAAAATAGA GAAAGTCTGG CTATAATTAA GTTGCAATCA CGAATTATCA
        TTTTTTATCT CTTTCAGACC GATATTAATT CAACGTTAGT GCTTAATAGT 60         70         80         90
              *          *          *          *
        TAAAAAAGGA GTGATAATTT ATG AAA TTT AAG TCA TTG ATT ACA
        ATTTTTTCCT CACTATTAAA TAC TTT AAA TTC AGT AAC TAA TGT
                                M   K   F   K   S   L   I   T 100         110        120        130
              *           *          *          *
        ACA ACA TTA GCA TTA GGC GTT ATA GCA TCA ACA GGA GCA AAC
        TGT TGT AAT CGT AAT CCG CAA TAT CGT AGT TGT CCT CGT TTG
         T   T   L   A   L   G   V   I   A   S   T   G   A   N 140        150        160        170
               *          *          *          *
        TTA GAT ACT AAC GAA GCA TCT GCC GCA GCT AAG CAA ATA GAT
        AAT CTA TGA TTG CTT CGT AGA CGG CGT CGA TTC GTT TAT CTA
         L   D   T   N   E   A   S   A   A   A   K   Q   I   D 180        190        200        210        220
          *          *          *          *          *
        AAA TCA TCA AGT TCA TTA CAC CAT GGA TAT TCT AAA ATA CAG
        TTT AGT AGT TCA AGT AAT GTG GTA CCT ATA AGA TTT TAT GTC
         K   S   S   S   S   L   H   H   G   Y   S   K   I   Q 230        240        250        260
                  *          *          *          *
        ATT CCA TAT ACA ATC ACT GTG AAT GGT ACA AGC CAA AAC ATT
        TAA GGT ATA TGT TAG TGA CAC TTA CCA TGT TCG GTT TTG TAA
         I   P   Y   T   I   T   V   N   G   T   S   Q   N   I
```

FIG. 2A

```
         270              280              290              300
          *                *                *                *
TTA TCA AGC TTA ACA TTT AAT AAG AAT CAA CAA ATT AGT TAT
AAT AGT TCG AAT TGT AAA TTA TTC TTA GTT GTT TAA TCA ATA
 L   S   S   L   T   F   N   K   N   Q   Q   I   S   Y 310              320              330              340
          *                *                *                *
AAA GAT ATA GAG AAT AAA GTT AAA TCA GTT TTA TAC TTT AAT
TTT CTA TAT CTC TTA TTT CAA TTT AGT CAA AAT ATG AAA TTA
 K   D   I   E   N   K   V   K   S   V   L   Y   F   N 350              360              370              380
          *                *                *                *
AGA GGT ATT AGT GAT ATC GAT TTA AGA CTT TCT AAG CAA GCA
TCT CCA TAA TCA CTA TAG CTA AAT TCT GAA AGA TTC GTT CGT
 R   G   I   S   D   I   D   L   R   L   S   K   Q   A 390              400              410              420              430
  *                *                *                *                *
AAA TAC ACG GTT CAT TTT AAG AAT GGA ACA AAA AGA GTT GTC
TTT ATG TGC CAA GTA AAA TTC TTA CCT TGT TTT TCT CAA CAG
 K   Y   T   V   H   F   K   N   G   T   K   R   V   V 440              450              460              470
             *                *                *                *
GAT TTG AAA GCA GGC ATT CAC ACA GCT GAC TTA ATC AAT ACA
CTA AAC TTT CGT CCG TAA GTG TGT CGA CTG AAT TAG TTA TGT
 D   L   K   A   G   I   H   T   A   D   L   I   N   T 480              490              500              510
             *                *                *                *
AGT GAC ATT AAA GCA ATT AGT GTT AAC GTA GAT ACT AAA AAG
TCA CTG TAA TTT CGT TAA TCA CAA TTG CAT CTA TGA TTT TTC
 S   D   I   K   A   I   S   V   N   V   D   T   K   K
```

FIG. 2B

```
            520             530             540             550
             *               *               *               *
CAA GTG AAA GAT AAA GAG GCA AAA GCA AAT GTT CAA GTG CCG
GTT CAC TTT CTA TTT CTC CGT TTT CGT TTA CAA GTT CAC GGC
 Q   V   K   D   K   E   A   K   A   N   V   Q   V   P 560             570             580             590
         *               *               *               *
TAT ACA ATC ACT GTG AAT GGT ACA AGC CAA AAC ATT TTA TCA
ATA TGT TAG TGA CAC TTA CCA TGT TCG GTT TTG TAA AAT AGT
 Y   T   I   T   V   N   G   T   S   Q   N   I   L   S 600             610             620             630             640
 *               *               *               *               *
AAC TTA ACA TTT AAA AAG AAT CAG CAA ATT AGT TAT AAA GAT
TTG AAT TGT AAA TTT TTC TTA GTC GTT TAA TCA ATA TTT CTA
 N   L   T   F   K   K   N   Q   Q   I   S   Y   K   D 650             660             670             680
             *               *               *               *
TTA GAG AAT AAT GTA AAA TCA GTT TTA AAA TCA AAC AGA GGT
AAT CTC TTA TTA CAT TTT AGT CAA AAT TTT AGT TTG TCT CCA
 L   E   N   N   V   K   S   V   L   K   S   N   R   G 690             700             710             720
             *               *               *               *
ATA ACT GAT GTA GAT TTA AGA CTT TCA AAA CAA GCG AAA TTT
TAT TGA CTA CAT CTA AAT TCT GAA AGT TTT GTT CGC TTT AAA
 I   T   D   V   D   L   R   L   S   K   Q   A   K   F
```

FIG. 2C

```
        730             740             750             760
         *               *               *               *
ACA GTT AAT TTT AAA AAT GGC ACG AAA AAA GTT ATC GAT TTG
TGT CAA TTA AAA TTT TTA CCG TGC TTT TTT CAA TAG CTA AAC
 T   V   N   F   K   N   G   T   K   K   V   I   D   L 770             780             790             800
         *               *               *               *
AAA GCA GGC ATT TAT ACA GCG AAC TTA ATC AAT ACA GGC GGT
TTT CGT CCG TAA ATA TGT CGC TTG AAT TAG TTA TGT CCG CCA
 K   A   G   I   Y   T   A   N   L   I   N   T   G   G 810             820             830             840             850
    *               *               *               *               *
ATT AAA AAT ATC AAT ATA AAT GTA GAA ACT AAA AAG CAA GCG
TAA TTT TTA TAG TTA TAT TTA CAT CTT TGA TTT TTC GTT CGC
 I   K   N   I   N   I   N   V   E   T   K   K   Q   A 860             870             880             890
             *               *               *               *
    AAA GAT AAA GAA GCA AAA GTA AAT AAT CAA GTG CCA TAT TCA
    TTT CTA TTT CTT CGT TTT CAT TTA TTA GTT CAC GGT ATA AGT
     K   D   K   E   A   K   V   N   N   Q   V   P   Y   S 900             910             920             930
         *               *               *               *
ATT AAT TTA AAT GGT ACA ACA ACT AAT ATT CAA TCT AAT TTA
TAA TTA AAT TTA CCA TGT TGT TGA TTA TAA GTT AGA TTA AAT
 I   N   L   N   G   T   T   T   N   I   Q   S   N   L 940             950             960             970
         *               *               *               *
GCA TTT TCA AAT AAA CCT TGG ACA AAT TAC AAA AAT TTA ACA
CGT AAA AGT TTA TTT GGA ACC TGT TTA ATG TTT TTA AAT TGT
 A   F   S   N   K   P   W   T   N   Y   K   N   L   T
```

FIG. 2D

```
       980            990           1000          1010
        *              *             *             *
ACA AAG GTA AAA TCA GTA TTG AAA TCT GAC AGA GGC GTT AGT
TGT TTC CAT TTT AGT CAT AAC TTT AGA CTG TCT CCG CAA TCA
 T   K   V   K   S   V   L   K   S   D   R   G   V   S 1020          1030          1040          1050          1060
    *             *             *             *             *
GAA CGT GAT TTG AAA CAC GCA AAG AAA GCG TAT TAC ACT GTT
CTT GCA CTA AAC TTT GTG CGT TTC TTT CGC ATA ATG TGA CAA
 E   R   D   L   K   H   A   K   K   A   Y   Y   T   V 1070          1080          1090          1100
           *             *             *             *
TAC TTT AAA AAT GGT GGT AAA AGA GTG ATA CAT TTA AAC TCG
ATG AAA TTT TTA CCA CCA TTT TCT CAC TAT GTA AAT TTG AGC
 Y   F   K   N   G   G   K   R   V   I   H   L   N   S 1110          1120          1130          1140
          *             *             *             *
AAT ATT TAT ACA GCT AAC TTA GTT CAT GCG AAA GAT GTT AAG
TTA TAA ATA TGT CGA TTG AAT CAA GTA CGC TTT CTA CAA TTC
 N   I   Y   T   A   N   L   V   H   A   K   D   V   K 1150          1160          1170          1180
          *             *             *             *
AGA ATT GAA GTT ACT GTA AAA ACA GTT TCG AAA GTA AAA GCG
TCT TAA CTT CAA TGA CAT TTT TGT CAA AGC TTT CAT TTT CGC
 R   I   E   V   T   V   K   T   V   S   K   V   K   A
```

FIG. 2E

```
         1190              1200              1210              1220
          *                 *                 *                 *
    GAG CGT TAT GTA CCA TAT ACA ATT GCA GTA AAT GGA GCA TCA
    CTC GCA ATA CAT GGT ATA TGT TAA CGT CAT TTA CCT CGT AGT
     E   R   Y   V   P   Y   T   I   A   V   N   G   A   S 1230              1240              1250              1260              1270
       *                 *                 *                 *                 *
    AAT CCA ACT TTA TCA GAT TTA AAA TTT ACA GGT GAC TCA CGT
    TTA GGT TGA AAT AGT CTA AAT TTT AAA TGT CCA CTG AGT GCA
     N   P   T   L   S   D   L   K   F   T   G   D   S   R 1280              1290              1300              1310
               *                 *                 *                 *
    GTA AGC TAC AGT GAT ATC AAG AAA AAA GTT AAA TCA GTA TTG
    CAT TCG ATG TCA CTA TAG TTC TTT TTT CAA TTT AGT CAT AAC
     V   S   Y   S   D   I   K   K   K   V   K   S   V   L 1320              1330              1340              1350
               *                 *                 *                 *
    AAA CAT GAT AGA GGT ATC GGT GAA CGT GAA TTA AAA TAT GCC
    TTT GTA CTA TCT CCA TAG CCA CTT GCA CTT AAT TTT ATA CGG
     K   H   D   R   G   I   G   E   R   E   L   K   Y   A 1360              1370              1380              1390
           *                 *                 *                 *
    GAA AAA GCA ACT TAT ACA GTA CAT TTT AAA AAT GGA ACA AAA
    CTT TTT CGT TGA ATA TGT CAT GTA AAA TTT TTA CCT TGT TTT
     E   K   A   T   Y   T   V   H   F   K   N   G   T   K 1400              1410              1420              1430
           *                 *                 *                 *
    AAA GTG ATT AAT TTA AAC TCT AAT ATT AGT CAA CTG AAT CTG
    TTT CAC TAA TTA AAT TTG AGA TTA TAA TCA GTT GAC TTA GAC
     K   V   I   N   L   N   S   N   I   S   Q   L   N   L
```

FIG. 2F

```
     1440           1450           1460           1470           1480
      *              *              *              *              *
CTT TAT GTC AAA GAT ATT AAA AAT ATA GAT ATC GAT GTT AAA
GAA ATA CAG TTT CTA TAA TTT TTA TAT CTA TAG CTA CAA TTT
 L   Y   V   K   D   I   K   N   I   D   I   D   V   K 1490           1500           1510           1520
             *              *              *              *
ACT GGG GCA AAA GCG AAA GTC TAT AGC TAT GTA CCA TAC ACA
TGA CCC CGT TTT CGC TTT CAG ATA TCG ATA CAT GGT ATG TGT
 T   G   A   K   A   K   V   Y   S   Y   V   P   Y   T 1530           1540           1550           1560
             *              *              *              *
ATC GCA GTA AAT GGG ACA ACA ACA CCT ATT GCA TCA AAA CTA
TAG CGT CAT TTA CCC TGT TGT TGT GGA TAA CGT AGT TTT GAT
 I   A   V   N   G   T   T   T   P   I   A   S   K   L 1570           1580           1590           1600
             *              *              *              *
AAA CTT TCG AAT AAA CAA TTA ATT GGT TAT CAA GAT TTA AAT
TTT GAA AGC TTA TTT GTT AAT TAA CCA ATA GTT CTA AAT TTA
 K   L   S   N   K   Q   L   I   G   Y   Q   D   L   N 1610           1620           1630           1640
             *              *              *              *
AAA AAA GTT AAA TCA GTT TTA AAA CAT GAT AGA GGT ATC AAT
TTT TTT CAA TTT AGT CAA AAT TTT GTA CTA TCT CCA TAG TTA
 K   K   V   K   S   V   L   K   H   D   R   G   I   N
```

FIG. 2G

```
      1650          1660          1670          1680          1690
        *             *             *             *             *
    GAT ATT GAA TTG AAA TTT GCG AAA CAA GCA AAG TAT ACT ATA
    CTA TAA CTT AAC TTT AAA CGC TTT GTT CGT TTC ATA TGA TAT
     D   I   E   L   K   F   A   K   Q   A   K   Y   T   I 1700          1710          1720          1730
                *             *             *             *
    CAC TTT AAA AAT GGA AAG ACA CAA GTC GTT GAC CTT AAA TCA
    GTG AAA TTT TTA CCT TTC TGT GTT CAG CAA CTG GAA TTT AGT
     H   F   K   N   G   K   T   Q   V   V   D   L   K   S 1740          1750          1760          1700
                *             *             *             *
    GAT ATC TTT ACA AGA AAT TTA TTC AGT GTC AAA GAT ATT AAA
    CTA TAG AAA TGT TCT TTA AAT AAG TCA CAG TTT CTA TAA TTT
     D   I   F   T   R   N   L   F   S   V   K   D   I   K 1780          1790          1800          1810
                *             *             *             *
    AAG ATT GAT ATT AAT GTG AAA CAA CAA TCT AAA TCT AAT AAA
    TTC TAA CTA TAA TTA CAC TTT GTT GTT AGA TTT AGA TTA TTT
     K   I   D   I   N   V   K   Q   Q   S   K   S   N   K 1820          1830          1840          1850
        *             *             *             *
    GCG CTT AAT AAA GTG ACT AAC AAA GCG ACT AAA GTG AAG TTT
    CGC GAA TTA TTT CAC TGA TTG TTT CGC TGA TTT CAC TTC AAA
     A   L   N   K   V   T   N   K   A   T   K   V   K   F 1860          1870          1880          1890          1900
        *             *             *             *             *
    CCA GTA ACG ATA AAT GGA TTT TCA AAT TTA GTT TCA AAT GAA
    GGT CAT TGC TAT TTA CCT AAA AGT TTA AAT CAA AGT TTA CTT
     P   V   T   I   N   G   F   S   N   L   V   S   N   E

FIG. 2H
```

```
         1910              1920              1930              1940
           *                 *                 *                 *
TTT GCG TTT TTA CAT CCA CAT AAA ATA ACA ACA AAC GAC TTG
AAA CGC AAA AAT GTA GGT GTA TTT TAT TGT TGT TTG CTG AAC
 F   A   F   L   H   P   H   K   I   T   T   N   D   L 1950              1960              1970              1980
           *                 *                 *                 *
AAT GCT AAA CTT AGA CTA GCG TTA CGA AGC GAT CAA GGT ATT
TTA CGA TTT GAA TCT GAT CGC AAT GCT TCG CTA GTT CCA TAA
 N   A   K   L   R   L   A   L   R   S   D   Q   G   I 1990              2000              2010              2020
           *                 *                 *                 *
ACT AAA CAT GAT ATT GGA CTT TCT GAA CGC ACT GTG TAT AAA
TGA TTT GTA CTA TAA CCT GAA AGA CTT GCG TGA CAC ATA TTT
 T   K   H   D   I   G   L   S   E   R   T   V   Y   K 2030              2040              2050              2060
        *                 *                 *                 *
GTG TAT TTT AAA GAC GGA TCA TCA AAA TTA GAA GAC TTA AAA
CAC ATA AAA TTT CTG CCT AGT AGT TTT AAT CTT CTG AAT TTT
 V   Y   F   K   D   G   S   S   K   L   E   D   L   K 2070              2080              2090              2100              2110
      *                 *                 *                 *                 *
GCT GCG AAA CAA GAT TCA AAA GTA TTT AAA GCA ACT GAC ATT
CGA CGC TTT GTT CTA AGT TTT CAT AAA TTT CGT TGA CTG TAA
 A   A   K   Q   D   S   K   V   F   K   A   T   D   I
```

FIG. 2I

```
              2120        2130        2140         2150
               *           *           *            *
       AAA AAA GTA GAC ATT GAA ATT AAA TTT TAA TCTTTAATTT
       TTT TTT CAT CTG TAA CTT TAA TTT AAA ATT AGAAATTAAA
        K   K   V   D   I   E   I   K   F   (SEQ ID NO:2)

2160        2170        2180        2190        2200
            *           *           *           *           *
       TATATTAAGG  CATCTCACAA  TAGTGGGGTG  CCTTTTACAT  TTGTAGAGAT
       ATATAATTCC  GTAGAGTGTT  ATCACCCCAC  GGAAAATGTA  AACATCTCTA 2210        2220        2230        2240        2250
            *           *           *           *           *
       GTGATACTTG  AAGTGATTTG  CCGCACGTTT  GATAAATTTA  TCTAAGGCAT
       CACTATGAAC  TTCACTAAAC  GGCGTGCAAA  CTATTTAAAT  AGATTCCGTA 2260        2270        2280        2290        2300
            *           *           *           *           *
       ATCAAGTTAT  GTTAGGAGAG  ATGTATAAAA  CTAATTAGGT  ATAGCGATTG
       TAGTTCAATA  CAATCCTCTC  TACATATTTT  GATTAATCCA  TATCGCTAAC 2310        2320        2330        2340        2350
            *           *           *           *           *
       ACAAGTTGCT  GAATAAAATA  TATCTTTTGA  TGCTTTGAAA  GAAGGAATAA
       TGTTCAACGA  CTTATTTTAT  ATAGAAAACT  ACGAAACTTT  CTTCCTTATT 2360        2370        2380        2390        2400
            *           *           *           *           *
       TTTTAAAAAT  AAAAAACCAA  TAATCCGAGT  CATACTCATC  AGATTATTGG
       AAAATTTTTA  TTTTTTGGTT  ATTAGGCTCA  GTATGAGTAG  TCTAATAACC
```

FIG. 2J

```
              2410       2420       2430
                *          *          *
         TTGAAATTAA TTATCTTAAG TCATCAATTC TTT     (SEQ ID NO:1)
         AACTTTAATT AATAGAATTC AGTAGTTAAG AAA
```

FIG. 2K

REPEATS    Bold letters = conserved aa residues + conservative changes

1    D-I-D-L-R-L-S-K-Q-A-K-Y-T-V-H-F-K-N-G-T-K-R-V-V-D-L-K-A-G-I-H (SEQ ID NO:3)
2    D-V-D-L-R-L-S-K-Q-A-K-F-T-V-N-F-K-N-G-T-K-K-V-I-D-L-K-A-G-I-Y (SEQ ID NO:4)
3    E-R-D-L-K-H-A-K-K-A-Y-Y-T-V-Y-F-K-N-G-G-K-R-V-I-H-L-N-S-N-I-Y (SEQ ID NO:5)
4    G-E-R-E-L-K-Y-A-E-K-A-T-Y-T-V-H-F-K-N-G-T-K-K-V-I-N-L-N-S-N-I-S (SEQ ID NO:6)
5    D-I-E-L-K-F-A-K-Q-A-K-Y-T-I-H-F-K-N-G-K-T-Q-V-V-D-L-K-S-D-I-F (SEQ ID NO:7)
6    K-H-D-I-G-L-S-E-R-T-V-Y-K-V-Y-F-K-D-G-S-S-K-L-E-D-L-K-A-A-K-Q (SEQ ID NO:8)

MHCII
HUMAN
HLA-DR-B1        Q-Q-D-K-Y-E-C-H-F-F-N-G-T-E-R-V-R-F-L-H-R-G-I-Y (SEQ ID NO:9)
HLA-DR-2         Q-Q-D-K-Y-E-C-H-F-F-N-G-T-E-R-V-R-F-L-H-R-G-I-Y (SEQ ID NO:10)
HLA-DR-B5 Dw22   Q-Q-D-K-Y-E-C-H-F-F-N-G-T-E-R-V-R-F-L-H-R-G-I-Y (SEQ ID NO:11)
HLA-D7    G-D-T-Q-P-R-F-L-E-Q-A-K-C-E-C-H-F-L-N-G-T-E-R-V-W-N-L (SEQ ID NO:12)
HLA-DR-9a D-T-Q-P-R-F-L-K-Q-D-K-F-E-C-H-F-F-N-G-T-E-R-V-R-Y-L-H-R-G-I-Y (SEQ ID NO:13)
HLADR9a   G-D-T-Q-P-R-F-L-E-Q-A-K-C-E-C-H-F-L-N-G-T-E-R-V-W-N-L (SEQ ID NO:14)
DRB1             R-F-L-K-Q-D-K-F-E-C-H-F-F-N-G-T-E-R-V-R-Y-L-H-R-G-I-Y (SEQ ID NO:15)
HLA-DRB1-0901Dw23 K-Q-D-K-F-E-C-H-F-F-N-G-T-E-R-V-R-Y-L-H-R-G-I-Y (SEQ ID NO:16)
HLA-DRB7         K-Q-D-K-F-E-C-H-F-F-N-G-T-E-R-V-R-Y-L-H-R-G-I-Y (SEQ ID NO:17)
HLA-DRB1         K-Q-D-K-F-E-C-Y-F-F-N-G-T-E-R-V-R-F-L-H-R-G-I-Y (SEQ ID NO:18)
DRB2Dw2a  D-T-R-P-R-F-L-Q-Q-D-K-Y-E-C-H-F-F-N-G-T-E-R-V-R-F-L-H-R-G-I-Y (SEQ ID NO:19)
DR2Dw2a   D-T-R-P-R-F-L-Q-Q-D-K-Y-E-C-H-F-F-N-G-T-E-R-V-R-F-L-H-R-D-I-Y (SEQ ID NO:20)
MONKEY
DR-B-5 PAN TROGLODYTES  K-Q-E-K-Y-E-C-H-F-F-N-G-T-E-R-V-R-F-L-H-R-G-I-Y (SEQ ID NO:21)
DR-B-5 PAN TROGLODYTES  K-Q-D-K-Y-E-C-H-F-F-N-G-T-E-R-V-R-Y-L-H-R-G-I-Y (SEQ ID NO:22)
MOUSE
H-2 E-1 B        R-F-L-E-Q-A-K-H-E-C-H-F-Y-N-G-T-Q-R-V-R-F-L-L-R-Q-I-H (SEQ ID NO:23)

FIG. 3

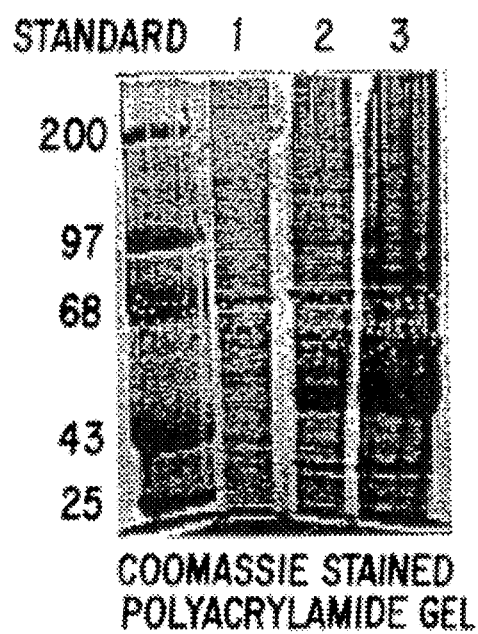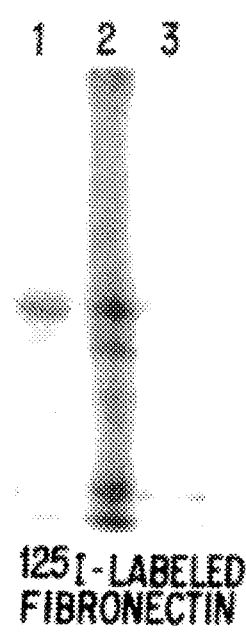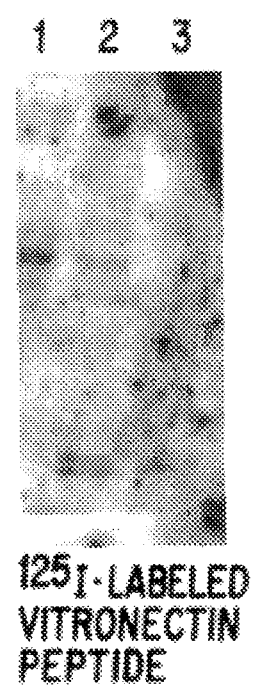
FIG. 5A COOMASSIE STAINED POLYACRYLAMIDE GEL
FIG. 5B 125I-LABELED FIBRONECTIN
FIG. 5C 125I-LABELED VITRONECTIN PEPTIDE

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 2433 base pairs
( B ) TYPE: nucleic acid
( C ) STRANDEDNESS: single -continued ( D ) TOPOLOGY: linear ( x i ) SEQUENCE DESCRIPTION: SEQ ID NO:1:

| | | | | | |
|---|---|---|---|---|---|
| AAAAAATAGA | GAAAGTCTGG | CTATAATTAA | GTTGCAATCA | CGAATTATCA | TAAAAAAGGA | 60 |
| GTGATAATTT | ATGAAATTTA | AGTCATTGAT | TACAACAACA | TTAGCATTAG | GCGTTATAGC | 120 |
| ATCAACAGGA | GCAAACTTAG | ATACTAACGA | AGCATCTGCC | GCAGCTAAGC | AAATAGATAA | 180 |
| ATCATCAAGT | TCATTACACC | ATGGATATTC | TAAAATACAG | ATTCCATATA | CAATCACTGT | 240 |
| GAATGGTACA | AGCCAAAACA | TTTTATCAAG | CTTAACATTT | AATAAGAATC | AACAAATTAG | 300 |
| TTATAAAGAT | ATAGAGAATA | AAGTTAAATC | AGTTTTATAC | TTTAATAGAG | GTATTAGTGA | 360 |
| TATCGATTTA | AGACTTTCTA | AGCAAGCAAA | ATACACGGTT | CATTTAAGA | ATGGAACAAA | 420 |
| AAGAGTTGTC | GATTTGAAAG | CAGGCATTCA | CACAGCTGAC | TTAATCAATA | CAAGTGACAT | 480 |
| TAAAGCAATT | AGTGTTAACG | TAGATACTAA | AAAGCAAGTG | AAAGATAAAG | AGGCAAAAGC | 540 |
| AAATGTTCAA | GTGCCGTATA | CAATCACTGT | GAATGGTACA | AGCCAAAACA | TTTTATCAAA | 600 |
| CTTAACATTT | AAAAAGAATC | AGCAAATTAG | TTATAAAGAT | TTAGAGAATA | ATGTAAAATC | 660 |
| AGTTTTAAAA | TCAAACAGAG | GTATAACTGA | TGTAGATTTA | AGACTTTCAA | ACAAGCGAA | 720 |
| ATTTACAGTT | AATTTTAAAA | ATGGCACGAA | AAAAGTTATC | GATTTGAAAG | CAGGCATTTA | 780 |
| TACAGCGAAC | TTAATCAATA | CAGGCGGTAT | TAAAAATATC | AATATAAATG | TAGAAACTAA | 840 |
| AAAGCAAGCG | AAAGATAAAG | AAGCAAAAGT | AAATAATCAA | GTGCCATATT | CAATTAATTT | 900 |
| AAATGGTACA | ACAACTAATA | TTCAATCTAA | TTAGCATTT | TCAAATAAAC | CTTGGACAAA | 960 |
| TTACAAAAAT | TTAACAACAA | AGGTAAAATC | AGTATTGAAA | TCTGACAGAG | GCGTTAGTGA | 1020 |
| ACGTGATTTG | AAACACGCAA | AGAAAGCGTA | TTACACTGTT | TACTTTAAAA | ATGGTGGTAA | 1080 |
| AAGAGTGATA | CATTTAAACT | CGAATATTTA | TACAGCTAAC | TTAGTTCATG | CGAAAGATGT | 1140 |
| TAAGAGAATT | GAAGTTACTG | TAAAAACAGT | TTCGAAAGTA | AAAGCGGAGC | GTTATGTACC | 1200 |
| ATATACAATT | GCAGTAAATG | GAGCATCAAA | TCCAACTTTA | TCAGATTTAA | AATTTACAGG | 1260 |
| TGACTCACGT | GTAAGCTACA | GTGATATCAA | GAAAAAAGTT | AAATCAGTAT | TGAAACATGA | 1320 |
| TAGAGGTATC | GGTGAACGTG | AATTAAAATA | TGCCGAAAAA | GCAACTTATA | CAGTACATTT | 1380 |
| TAAAAATGGA | ACAAAAAAAG | TGATTAATTT | AAACTCTAAT | ATTAGTCAAC | TGAATCTGCT | 1440 |
| TTATGTCAAA | GATATTAAAA | ATATAGATAT | CGATGTTAAA | ACTGGGGCAA | AAGCGAAAGT | 1500 |
| CTATAGCTAT | GTACCATACA | CAATCGCAGT | AAATGGGACA | ACAACACCTA | TTGCATCAAA | 1560 |
| ACTAAAACTT | TCGAATAAAC | AATTAATTGG | TTATCAAGAT | TTAAATAAAA | AAGTTAAATC | 1620 |
| AGTTTAAAA | CATGATAGAG | GTATCAATGA | TATTGAATTG | AAATTTGCGA | ACAAGCAAA | 1680 |
| GTATACTATA | CACTTTAAAA | ATGGAAAGAC | ACAAGTCGTT | GACCTTAAAT | CAGATATCTT | 1740 |
| TACAAGAAAT | TTATTCAGTG | TCAAAGATAT | TAAAAGATT | GATATTAATG | TGAAACAACA | 1800 |
| ATCTAAATCT | AATAAAGCGC | TTAATAAAGT | GACTAACAAA | GCGACTAAAG | TGAAGTTTCC | 1860 |
| AGTAACGATA | AATGGATTTT | CAAATTTAGT | TTCAAATGAA | TTTGCGTTTT | TACATCCACA | 1920 |
| TAAAATAACA | ACAAACGACT | TGAATGCTAA | ACTTAGACTA | GCGTTACGAA | GCGATCAAGG | 1980 |
| TATTACTAAA | CATGATATTG | GACTTTCTGA | ACGCACTGTG | TATAAAGTGT | ATTTTAAAGA | 2040 |
| CGGATCATCA | AAATTAGAAG | ACTTAAAAGC | TGCGAAACAA | GATTCAAAAG | TATTTAAAGC | 2100 |
| AACTGACATT | AAAAAAGTAG | ACATTGAAAT | TAAATTTTAA | TCTTTAATTT | TATATTAAGG | 2160 |
| CATCTCACAA | TAGTGGGGTG | CCTTTTACAT | TTGTAGAGAT | GTGATACTTG | AAGTGATTTG | 2220 |
| CCGCACGTTT | GATAAATTTA | TCTAAGGCAT | ATCAAGTTAT | GTTAGGAGAG | ATGTATAAAA | 2280 |

```
CTAATTAGGT ATAGCGATTG ACAAGTTGCT GAATAAAATA TATCTTTTGA TGCTTTGAAA        2340

GAAGGAATAA TTTTAAAAAT AAAAAACCAA TAATCCGAGT CATACTCATC AGATTATTGG        2400

TTGAAATTAA TTATCTTAAG TCATCAATTC TTT                                     2433
```

( 2 ) INFORMATION FOR SEQ ID NO:2:

( i ) SEQUENCE CHARACTERISTICS:
        ( A ) LENGTH: 689 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Met  Lys  Phe  Lys  Ser  Leu  Ile  Thr  Thr  Thr  Leu  Ala  Leu  Gly  Val  Ile
 1              5                        10                       15

Ala  Ser  Thr  Gly  Ala  Asn  Leu  Asp  Thr  Asn  Glu  Ala  Ser  Ala  Ala  Ala
              20                        25                       30

Lys  Gln  Ile  Asp  Lys  Ser  Ser  Ser  Leu  His  His  Gly  Tyr  Ser  Lys
         35                        40                       45

Ile  Gln  Ile  Pro  Tyr  Thr  Ile  Thr  Val  Asn  Gly  Thr  Ser  Gln  Asn  Ile
         50                        55                       60

Leu  Ser  Ser  Leu  Thr  Phe  Asn  Lys  Asn  Gln  Gln  Ile  Ser  Tyr  Lys  Asp
 65                       70                        75                       80

Ile  Glu  Asn  Lys  Val  Lys  Ser  Val  Leu  Tyr  Phe  Asn  Arg  Gly  Ile  Ser
                   85                        90                       95

Asp  Ile  Asp  Leu  Arg  Leu  Ser  Lys  Gln  Ala  Lys  Tyr  Thr  Val  His  Phe
              100                       105                      110

Lys  Asn  Gly  Thr  Lys  Arg  Val  Val  Asp  Leu  Lys  Ala  Gly  Ile  His  Thr
              115                       120                      125

Ala  Asp  Leu  Ile  Asn  Thr  Ser  Asp  Ile  Lys  Ala  Ile  Ser  Val  Asn  Val
         130                       135                      140

Asp  Thr  Lys  Lys  Gln  Val  Lys  Asp  Lys  Glu  Ala  Lys  Ala  Asn  Val  Gln
145                       150                       155                      160

Val  Pro  Tyr  Thr  Ile  Thr  Val  Asn  Gly  Thr  Ser  Gln  Asn  Ile  Leu  Ser
                   165                       170                      175

Asn  Leu  Thr  Phe  Lys  Lys  Asn  Gln  Gln  Ile  Ser  Tyr  Lys  Asp  Leu  Glu
              180                       185                      190

Asn  Asn  Val  Lys  Ser  Val  Leu  Lys  Ser  Asn  Arg  Gly  Ile  Thr  Asp  Val
         195                       200                      205

Asp  Leu  Arg  Leu  Ser  Lys  Gln  Ala  Lys  Phe  Thr  Val  Asn  Phe  Lys  Asn
210                       215                       220

Gly  Thr  Lys  Lys  Val  Ile  Asp  Leu  Lys  Ala  Gly  Ile  Tyr  Thr  Ala  Asn
225                       230                       235                      240

Leu  Ile  Asn  Thr  Gly  Gly  Ile  Lys  Asn  Ile  Asn  Ile  Asn  Val  Glu  Thr
                   245                       250                      255

Lys  Lys  Gln  Ala  Lys  Asp  Lys  Glu  Ala  Lys  Val  Asn  Asn  Gln  Val  Pro
              260                       265                      270

Tyr  Ser  Ile  Asn  Leu  Asn  Gly  Thr  Thr  Asn  Ile  Gln  Ser  Asn  Leu
         275                       280                      285

Ala  Phe  Ser  Asn  Lys  Pro  Trp  Thr  Asn  Tyr  Lys  Asn  Leu  Thr  Thr  Lys
         290                       295                      300

Val  Lys  Ser  Val  Leu  Lys  Ser  Asp  Arg  Gly  Val  Ser  Glu  Arg  Asp  Leu
305                       310                       315                      320

Lys  His  Ala  Lys  Lys  Ala  Tyr  Tyr  Thr  Val  Tyr  Phe  Lys  Asn  Gly  Gly
                   325                       330                      335
```

| | | | | | | | | | | | | | | | |
|---|---|---|---|---|---|---|---|---|---|---|---|---|---|---|---|
| Lys | Arg | Val | Ile 340 | His | Leu | Asn | Ser | Asn 345 | Ile | Tyr | Thr | Ala | Asn 350 | Leu | Val |
| His | Ala | Lys 355 | Asp | Val | Lys | Arg | Ile 360 | Glu | Val | Thr | Val | Lys 365 | Thr | Val | Ser |
| Lys | Val 370 | Lys | Ala | Glu | Arg | Tyr 375 | Val | Pro | Tyr | Thr | Ile 380 | Ala | Val | Asn | Gly |
| Ala 385 | Ser | Asn | Pro | Thr | Leu 390 | Ser | Asp | Leu | Lys | Phe 395 | Thr | Gly | Asp | Ser | Arg 400 |
| Val | Ser | Tyr | Ser | Asp 405 | Ile | Lys | Lys | Val | Lys 410 | Ser | Val | Leu | Lys 415 | His | |
| Asp | Arg | Gly | Ile 420 | Gly | Glu | Arg | Glu | Leu 425 | Lys | Tyr | Ala | Glu | Lys 430 | Ala | Thr |
| Tyr | Thr | Val 435 | His | Phe | Lys | Asn | Gly 440 | Thr | Lys | Lys | Val | Ile 445 | Asn | Leu | Asn |
| Ser | Asn 450 | Ile | Ser | Gln | Leu | Asn 455 | Leu | Leu | Tyr | Val | Lys 460 | Asp | Ile | Lys | Asn |
| Ile 465 | Asp | Ile | Asp | Val | Lys 470 | Thr | Gly | Ala | Lys | Ala 475 | Lys | Val | Tyr | Ser | Tyr 480 |
| Val | Pro | Tyr | Thr | Ile 485 | Ala | Val | Asn | Gly | Thr 490 | Thr | Thr | Pro | Ile | Ala 495 | Ser |
| Lys | Leu | Lys | Leu 500 | Ser | Asn | Lys | Gln | Leu 505 | Ile | Gly | Tyr | Gln | Asp 510 | Leu | Asn |
| Lys | Lys | Val 515 | Lys | Ser | Val | Leu | Lys 520 | His | Asp | Arg | Gly | Ile 525 | Asn | Asp | Ile |
| Glu | Leu 530 | Lys | Phe | Ala | Lys | Gln 535 | Ala | Lys | Tyr | Thr | Ile 540 | His | Phe | Lys | Asn |
| Gly 545 | Lys | Thr | Gln | Val | Val 550 | Asp | Leu | Lys | Ser | Asp 555 | Ile | Phe | Thr | Arg | Asn 560 |
| Leu | Phe | Ser | Val | Lys 565 | Asp | Ile | Lys | Lys | Ile 570 | Asp | Ile | Asn | Val | Lys 575 | Gln |
| Gln | Ser | Lys | Ser 580 | Asn | Lys | Ala | Leu | Asn 585 | Lys | Val | Thr | Asn | Lys 590 | Ala | Thr |
| Lys | Val | Lys 595 | Phe | Pro | Val | Thr | Ile 600 | Asn | Gly | Phe | Ser | Asn 605 | Leu | Val | Ser |
| Asn | Glu 610 | Phe | Ala | Phe | Leu | His 615 | Pro | His | Lys | Ile | Thr 620 | Thr | Asn | Asp | Leu |
| Asn 625 | Ala | Lys | Leu | Arg | Leu 630 | Ala | Leu | Arg | Ser | Asp 635 | Gln | Gly | Ile | Thr | Lys 640 |
| His | Asp | Ile | Gly | Leu 645 | Ser | Glu | Arg | Thr | Val 650 | Tyr | Lys | Val | Tyr | Phe 655 | Lys |
| Asp | Gly | Ser | Ser 660 | Lys | Leu | Glu | Asp | Leu 665 | Lys | Ala | Ala | Lys | Gln 670 | Asp | Ser |
| Lys | Val | Phe 675 | Lys | Ala | Thr | Asp | Ile 680 | Lys | Lys | Val | Asp | Ile 685 | Glu | Ile | Lys |
| Phe | | | | | | | | | | | | | | | |

( 2 ) INFORMATION FOR SEQ ID NO:3:

( i ) SEQUENCE CHARACTERISTICS:
        ( A ) LENGTH: 31 amino acids
        ( B ) TYPE: amino acid
        ( C ) STRANDEDNESS:
        ( D ) TOPOLOGY: linear ( x i ) SEQUENCE DESCRIPTION: SEQ ID NO:3:

Asp   Ile   Asp   Leu   Arg   Leu   Ser   Lys   Gln   Ala   Lys   Tyr   Thr   Val   His   Phe 5,648,240

| 1 | | | | 5 | | | | | 10 | | | | | 15 |
|---|---|---|---|---|---|---|---|---|---|---|---|---|---|---|

Lys Asn Gly Thr Lys Arg Val Val Asp Leu Lys Ala Gly Ile His
                20                      25                      30

( 2 ) INFORMATION FOR SEQ ID NO:4:

( i ) SEQUENCE CHARACTERISTICS:
        ( A ) LENGTH: 31 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

Asp Val Asp Leu Arg Leu Ser Lys Gln Ala Lys Phe Thr Val Asn Phe
1                       5                       10                      15

Lys Asn Gly Thr Lys Lys Val Ile Asp Leu Lys Ala Gly Ile Tyr
                20                      25                      30

( 2 ) INFORMATION FOR SEQ ID NO:5:

( i ) SEQUENCE CHARACTERISTICS:
        ( A ) LENGTH: 31 amino acids
        ( B ) TYPE: amino acid
        ( C ) STRANDEDNESS:
        ( D ) TOPOLOGY: linear ( x i ) SEQUENCE DESCRIPTION: SEQ ID NO:5:

Glu Arg Asp Leu Lys His Ala Lys Lys Ala Tyr Tyr Thr Val Tyr Phe
1                       5                       10                      15

Lys Asn Gly Gly Lys Arg Val Ile His Leu Asn Ser Asn Ile Tyr
                20                      25                      30

( 2 ) INFORMATION FOR SEQ ID NO:6:

( i ) SEQUENCE CHARACTERISTICS:
        ( A ) LENGTH: 32 amino acids
        ( B ) TYPE: amino acid
        ( C ) STRANDEDNESS:
        ( D ) TOPOLOGY: linear ( x i ) SEQUENCE DESCRIPTION: SEQ ID NO:6:

Gly Glu Arg Glu Leu Lys Tyr Ala Glu Lys Ala Thr Tyr Thr Val His
1                       5                       10                      15

Phe Lys Asn Gly Thr Lys Lys Val Ile Asn Leu Asn Ser Asn Ile Ser
                20                      25                      30

( 2 ) INFORMATION FOR SEQ ID NO:7:

( i ) SEQUENCE CHARACTERISTICS:
        ( A ) LENGTH: 31 amino acids
        ( B ) TYPE: amino acid
        ( C ) STRANDEDNESS:
        ( D ) TOPOLOGY: linear ( x i ) SEQUENCE DESCRIPTION: SEQ ID NO:7:

Asp Ile Glu Leu Lys Phe Ala Lys Gln Ala Lys Tyr Thr Ile His Phe
1                       5                       10                      15

Lys Asn Gly Lys Thr Gln Val Val Asp Leu Lys Ser Asp Ile Phe
                20                      25                      30

( 2 ) INFORMATION FOR SEQ ID NO:8:

( i ) SEQUENCE CHARACTERISTICS:
        ( A ) LENGTH: 31 amino acids
        ( B ) TYPE: amino acid
        ( C ) STRANDEDNESS:

( D ) TOPOLOGY: linear ( x i ) SEQUENCE DESCRIPTION: SEQ ID NO:8:

Lys His Asp Ile Gly Leu Ser Glu Arg Thr Val Tyr Lys Val Tyr Phe
1               5                   10                  15

Lys Asp Gly Ser Ser Lys Leu Glu Asp Leu Lys Ala Ala Lys Gln
            20              25                  30

( 2 ) INFORMATION FOR SEQ ID NO:9:

( i ) SEQUENCE CHARACTERISTICS:
      ( A ) LENGTH: 24 amino acids
      ( B ) TYPE: amino acid
      ( C ) STRANDEDNESS:
      ( D ) TOPOLOGY: linear ( x i ) SEQUENCE DESCRIPTION: SEQ ID NO:9:

Gln Gln Asp Lys Tyr Glu Cys His Phe Phe Asn Gly Thr Glu Arg Val
1               5                   10                  15

Arg Phe Leu His Arg Gly Ile Tyr
            20

( 2 ) INFORMATION FOR SEQ ID NO:10:

( i ) SEQUENCE CHARACTERISTICS:
      ( A ) LENGTH: 24 amino acids
      ( B ) TYPE: amino acid
      ( C ) STRANDEDNESS:
      ( D ) TOPOLOGY: linear ( x i ) SEQUENCE DESCRIPTION: SEQ ID NO:10:

Gln Gln Asp Lys Tyr Glu Cys His Phe Phe Asn Gly Thr Glu Arg Val
1               5                   10                  15

Arg Phe Leu His Arg Gly Ile Tyr
            20

( 2 ) INFORMATION FOR SEQ ID NO:11:

( i ) SEQUENCE CHARACTERISTICS:
      ( A ) LENGTH: 24 amino acids
      ( B ) TYPE: amino acid
      ( C ) STRANDEDNESS:
      ( D ) TOPOLOGY: linear ( x i ) SEQUENCE DESCRIPTION: SEQ ID NO:11:

Gln Gln Asp Lys Tyr Glu Cys His Phe Phe Asn Gly Thr Glu Arg Val
1               5                   10                  15

Arg Phe Leu His Arg Gly Ile Tyr
            20

( 2 ) INFORMATION FOR SEQ ID NO:12:

( i ) SEQUENCE CHARACTERISTICS:
      ( A ) LENGTH: 27 amino acids
      ( B ) TYPE: amino acid
      ( C ) STRANDEDNESS:
      ( D ) TOPOLOGY: linear ( x i ) SEQUENCE DESCRIPTION: SEQ ID NO:12:

Gly Asp Thr Gln Pro Arg Phe Leu Glu Gln Ala Lys Cys Glu Cys His
1               5                   10                  15

Phe Leu Asn Gly Thr Glu Arg Val Trp Asn Leu
            20                  25

( 2 ) INFORMATION FOR SEQ ID NO:13:

( i ) SEQUENCE CHARACTERISTICS:
  ( A ) LENGTH: 31 amino acids
  ( B ) TYPE: amino acid
  ( C ) STRANDEDNESS:
  ( D ) TOPOLOGY: linear ( x i ) SEQUENCE DESCRIPTION: SEQ ID NO:13:

Asp Thr Gln Pro Arg Phe Leu Lys Gln Asp Lys Phe Glu Cys His Phe
1               5                   10                  15

Phe Asn Gly Thr Glu Arg Val Arg Tyr Leu His Arg Gly Ile Tyr
            20                  25                  30

( 2 ) INFORMATION FOR SEQ ID NO:14:

( i ) SEQUENCE CHARACTERISTICS:
    ( A ) LENGTH: 27 amino acids
    ( B ) TYPE: amino acid
    ( C ) STRANDEDNESS:
    ( D ) TOPOLOGY: linear ( x i ) SEQUENCE DESCRIPTION: SEQ ID NO:14:

Gly Asp Thr Gln Pro Arg Phe Leu Glu Gln Ala Lys Cys Glu Cys His
1               5                   10                  15

Phe Leu Asn Gly Thr Glu Arg Val Trp Asn Leu
            20                  25

( 2 ) INFORMATION FOR SEQ ID NO:15:

( i ) SEQUENCE CHARACTERISTICS:
    ( A ) LENGTH: 27 amino acids
    ( B ) TYPE: amino acid
    ( C ) STRANDEDNESS:
    ( D ) TOPOLOGY: linear ( x i ) SEQUENCE DESCRIPTION: SEQ ID NO:15:

Arg Phe Leu Lys Gln Asp Lys Phe Glu Cys His Phe Phe Asn Gly Thr
1               5                   10                  15

Glu Arg Val Arg Tyr Leu His Arg Gly Ile Tyr
            20                  25

( 2 ) INFORMATION FOR SEQ ID NO:16:

( i ) SEQUENCE CHARACTERISTICS:
    ( A ) LENGTH: 24 amino acids
    ( B ) TYPE: amino acid
    ( C ) STRANDEDNESS:
    ( D ) TOPOLOGY: linear ( x i ) SEQUENCE DESCRIPTION: SEQ ID NO:16:

Lys Gln Asp Lys Phe Glu Cys His Phe Phe Asn Gly Thr Glu Arg Val
1               5                   10                  15

Arg Tyr Leu His Arg Gly Ile Tyr
            20

( 2 ) INFORMATION FOR SEQ ID NO:17:

( i ) SEQUENCE CHARACTERISTICS:
    ( A ) LENGTH: 24 amino acids
    ( B ) TYPE: amino acid
    ( C ) STRANDEDNESS:
    ( D ) TOPOLOGY: linear ( x i ) SEQUENCE DESCRIPTION: SEQ ID NO:17:

Lys Gln Asp Lys Phe Glu Cys His Phe Phe Asn Gly Thr Glu Arg Val
1               5                   10                  15

```
             Arg    Tyr    Leu    His    Arg    Gly    Ile    Tyr
                                   20
```

( 2 ) INFORMATION FOR SEQ ID NO:18:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( x i ) SEQUENCE DESCRIPTION: SEQ ID NO:18:

```
    Lys    Gln    Asp    Lys    Phe    Glu    Cys    Tyr    Phe    Asn    Gly    Thr    Glu    Arg    Val
    1                            5                                  10                                  15

Arg    Tyr    Leu    His    Arg    Gly    Ile    Tyr
                                 20
```

( 2 ) INFORMATION FOR SEQ ID NO:19:

( i ) SEQUENCE CHARACTERISTICS:
        ( A ) LENGTH: 31 amino acids
        ( B ) TYPE: amino acid
        ( C ) STRANDEDNESS:
        ( D ) TOPOLOGY: linear ( x i ) SEQUENCE DESCRIPTION: SEQ ID NO:19:

```
    Asp    Thr    Arg    Pro    Arg    Phe    Leu    Gln    Gln    Asp    Lys    Tyr    Glu    Cys    His    Phe
    1                            5                                  10                                  15

Phe    Asn    Gly    Thr    Glu    Arg    Val    Arg    Phe    Leu    His    Arg    Gly    Ile    Tyr
                          20                                  25                                  30
```

( 2 ) INFORMATION FOR SEQ ID NO:20:

( i ) SEQUENCE CHARACTERISTICS:
        ( A ) LENGTH: 31 amino acids
        ( B ) TYPE: amino acid
        ( C ) STRANDEDNESS:
        ( D ) TOPOLOGY: linear ( x i ) SEQUENCE DESCRIPTION: SEQ ID NO:20:

```
    Asp    Thr    Arg    Pro    Arg    Phe    Leu    Gln    Gln    Asp    Lys    Tyr    Glu    Cys    His    Phe
    1                            5                                  10                                  15

Phe    Asn    Gly    Thr    Glu    Arg    Val    Arg    Phe    Leu    His    Arg    Asp    Ile    Tyr
                          20                                  25                                  30
```

( 2 ) INFORMATION FOR SEQ ID NO:21:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( x i ) SEQUENCE DESCRIPTION: SEQ ID NO:21:

```
    Lys    Gln    Glu    Lys    Tyr    Glu    Cys    His    Phe    Phe    Asn    Gly    Thr    Glu    Arg    Val
    1                            5                                  10                                  15

Arg    Phe    Leu    His    Arg    Gly    Ile    Tyr
                                 20
```

( 2 ) INFORMATION FOR SEQ ID NO:22:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear (x i) SEQUENCE DESCRIPTION: SEQ ID NO:22:

Lys Gln Asp Lys Tyr Glu Cys His Phe Phe Asn Gly Thr Glu Arg Val
1               5                   10                  15

Arg Tyr Leu His Arg Gly Ile Tyr
                20

(2) INFORMATION FOR SEQ ID NO:23:

(i) SEQUENCE CHARACTERISTICS:
   (A) LENGTH: 27 amino acids
   (B) TYPE: amino acid
   (C) STRANDEDNESS:
   (D) TOPOLOGY: linear (x i) SEQUENCE DESCRIPTION: SEQ ID NO:23:

Arg Phe Leu Glu Gln Ala Lys His Glu Cys His Phe Tyr Asn Gly Thr
1               5                   10                  15

Gln Arg Val Arg Phe Leu Leu Arg Gln Ile His
                20                  25

(2) INFORMATION FOR SEQ ID NO:24:

(i) SEQUENCE CHARACTERISTICS:
   (A) LENGTH: 27 base pairs
   (B) TYPE: nucleic acid
   (C) STRANDEDNESS: single
   (D) TOPOLOGY: linear (x i) SEQUENCE DESCRIPTION: SEQ ID NO:24:

CGGGATCCGC AGCTAAGCAA ATAGATA                                    27

(2) INFORMATION FOR SEQ ID NO:25:

(i) SEQUENCE CHARACTERISTICS:
   (A) LENGTH: 27 base pairs
   (B) TYPE: nucleic acid
   (C) STRANDEDNESS: single
   (D) TOPOLOGY: linear (x i) SEQUENCE DESCRIPTION: SEQ ID NO:25:

GCGTCGACGC GGCAAATCAC TTCAAGT                                    27

MHC II ANALOG FROM *STAPHYLOCOCCUS AUREUS*

The United States government has certain rights in the present invention pursuant to Grant No. HL-47313 from the National Institutes of Health.

BACKGROUND OF THE INVENTION

Development of new antimicrobial agents and improved public health conditions have not substantially reduced the frequency of infections caused by *Staphylococcus aureus*. Staphylococci are the leading cause of osteomyelitis, septic arthritis, endocarditis, wound and foreign body infections. What constitutes the challenge in the treatment of staphylococcal infections is that staphylococci may resist treatment with conventional antimicrobial agents because of difficulties in achieving and maintaining therapeutically active concentrations of antibiotics in tissues which are either poorly vascularized (like bone) or harbor colonies of bacteria where diffusion is impaired (such as biofilms on surgical implants). Paradoxically, advances in the field of medical therapy have contributed to a steady increase of in the number of infections caused by coagulase-positive and -negative staphylococci by creating more situations in which these opportunistic pathogens find a suitable environment to multiply.

First described by Ogston more than a century ago, *S. aureus* has remained a mysterious pathogen. It is obvious that its virulence is multifactorial, and related to the production of a wide variety of extracellular and cell surface bound pathogenicity factors. The relative importance of these factors may vary depending on the site and stage of an infection, and various models have been proposed to explain the roles of individual factors. The most effective way to prevent an infection is early in the process of infection, before bacteria manage to multiply.

The concept of preventing infection by interfering with the initial microbial adherence to the host tissue is in this context particularly appealing. The molecular mechanisms of microbial adherence have been extensively studied for many Gram-negative bacteria, and only in the last decade shed some light on possible adhesion mechanisms of Gram-positive bacteria. Historically speaking, the association of *S. aureus* with fibrinogen (mediated by what was subsequently termed clumping factor, or less correctly, bound coagulase) described by Much in 1908 appears to be the first description of a putative adherence mechanism.

When Kuusela described binding of *S. aureus* cells to the then newly rediscovered fibronectin, a new chapter in the study of *S. aureus* adherence was opened (Kuusela, P., et al., *Nature* 276:718–720 (1978)). Soon, many other observations followed, indicating that 1) fibronectin may be recognized by many different bacteria, both Gram-positive and Gram-negative, and 2) in addition to fibronectin, many other connective tissue proteins are recognized and bound by bacteria. Currently the rate of description of new interactions between bacteria and connective tissue components, or eukaryotic cell surface components like integrins, seems to be limited only by the rate at which these components are discovered.

In addition to fibrinogen and fibronectin, *S. aureus* strains associate with several other adhesive eukaryotic proteins (many of which belong to the family of adhesive matrix proteins)—laminin (Lopes et al., *Science* 229:275–277 (1985)), vitronectin (Chhatwal, G. S., et al, *Infect Immun.* 55:1878–1883 (1987)), bone sialoprotein (Ryden, C., et al., *Eur. J. Biochem.* 184:331–336 (1989)), proteoglycans (Ryden et al., 1989), endothelial cell membrane protein (Tompkins, D.C., et al., *J. Clin. Invest.* 85:1323–1327 (1990)) and collagens. These interactions have mostly been studied in systems in which either soluble host proteins or microparticles coated with these proteins are incubated with bacteria. Indications that these bacteria-protein interactions play a role in virulence have been demonstrated in only few instances. Progress in this field has been relatively slow and may require a detailed knowledge of the bacterial components that serve as receptors for the matrix proteins.

As reported in the Apr. 15, 1994 edition of Science, for several years now, medical microbiologists have been tracking an alarming trend in microbial infection. It has been found that antibiotics that once killed bacterial pathogens with ease are becoming ineffective. This is the result of the remarkable ability of bacteria eventually to develop resistance to virtually every antibiotic medical research has utilized against them. Particularly worrisome is the relative dearth of new antibiotics on the horizon. And of the new antibiotics proposed, few employ novel modes of action that would be more difficult for bacteria to circumvent. Researchers and manufacturers have assumed that they have solved the problem of bacterial infection—after all, the market consists of over 100 antibiotics—and many pharmaceutical firms and research organizations have abandoned work on antibiotics or refused to fund these projects.

There are today strains of Staphylococcus which often cause fatal hospital infections that are immune to all but one existing antibiotic. It is predicted that it will not be long before that final barrier will fall.

SUMMARY OF THE INVENTION

An object of the present invention is to provide the nucleotide sequence of an MHC II-antigen protein analog gene from *Staphylococcus aureus*.

A further object of the present invention is the provision of the amino acid sequence of an MHC II-antigen protein analog from *Staphylococcus aureus*.

Another object of the present invention is to provide a vaccine for inhibiting staphylococcal infections.

An additional object of the present invention is to provide a method for using the MHC II-antigen protein analog from *Staphylococcus aureus* as an in vivo vaccine for inhibiting staphylococcal infections.

A further object of the present invention is to provide a method for using derivatives of the MHC II-antigen protein analog from *Staphylococcus aureus* as an in vivo vaccine for inhibiting staphylococcal infections.

An additional object of the present invention is a method for vaccine production in humans or in animals.

Thus, in accomplishing the foregoing objects, there is provided in accordance with one aspect of the present invention the nucleotide sequence for gene for the MHC II-antigen protein analog from *Staphylococcus aureus*, and the amino acid sequence for the MHC II-antigen protein analog from *Staphylococcus aureus*.

In accomplishing an additional object, there further is provided in accordance with the present invention an in vivo vaccine comprising the entire MHC II antigen protein, or fragments of the protein, alone or in combination with other *S. aureus* antigens, necessary for the elicitation of therapeutically active antibodies.

In a specific embodiment of the present invention, there is provided derivatives of the MHC II-antigen protein analog from Staphylococcus to be used as an in vivo vaccine comprising an intact version of the polypeptide, or biologically active subfragments, alone or in a mixture with other antigens from Gram-positive organisms.

In an additional embodiment of the present invention, there is provided a method for using the MHC II-antigen protein analog from Staphylococcus or its derivatives as an in vivo vaccine comprising the steps of expression of the MHC II antigen analog protein in a recombinant system, purification to homogeneity, and immunization using the protein in a pharmaceutically acceptable dispensing agent. Different routes of immunization may be used and various adjuvants may be added so that optimal dosage can be achieved. In order to obtain sufficient levels of antigen in the body, multiple injections will be used. Additionally, passive immunization of affected individuals is used if needed.

Other and further objects, features and advantages will be apparent and the invention more readily understood from a reading of the following specification and by reference to the accompanying drawings forming a part thereof, wherein the examples of the presently preferred embodiments of the invention are given for the purposes of disclosure.

DESCRIPTION OF THE DRAWINGS

FIGS. 2A–2K show the entire nucleotide sequence of the gene and the deduced amino acid sequence. Nucleic acid sequence IDs numbers 1 and 2 are indicated.

FIG. 3 represents a comparison of the subsegment of the repeat units in the staphylococcal protein and various MHC II sequences. Amino acid Sequence IDs 3 through 8 are indicated.

FIG. 5A, FIG. 5B, and FIG. 5C show the binding of radiolabelled fibronectin and a radiolabelled synthetic peptide (mimicking a vitronectin (Vn) sequence) to the native protein purified as shown, as well as to recombinant version of the protein expressed in E. coli. Lane 1 shows native S. aureus LiCl purified protein, lane 2 is sonicated recombinant E. coli clone and lane 3 is sonicated E. coli without S. aureus gene.

DETAILED DESCRIPTION OF THE INVENTION

Figure 1:
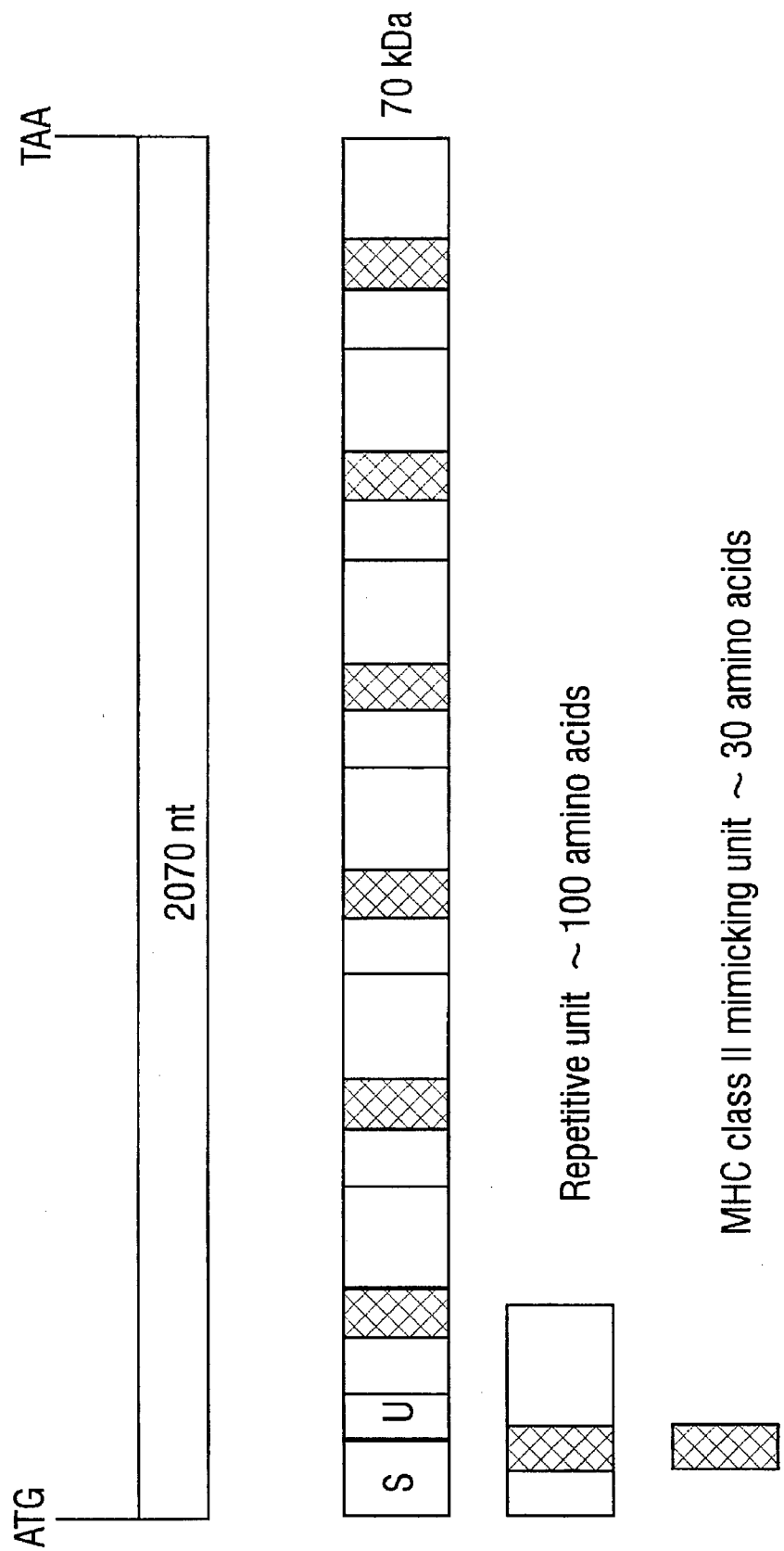
FIG. 1 shows the gene encoding the MHC II-antigen like staphylococcal protein as well as the protein based on the deduced amino acid sequence. The gene is comprised of 2070 nucleotides and codes for a signal sequence (S) that is 30 amino acids long, a segment with a unique sequence (U), and six repeated segments of 100 amino acids each. The six segments contain a subsegment that is 30 amino acids in length and that has a high degree of similarity with various MHC class II antigens.
Figure 4:
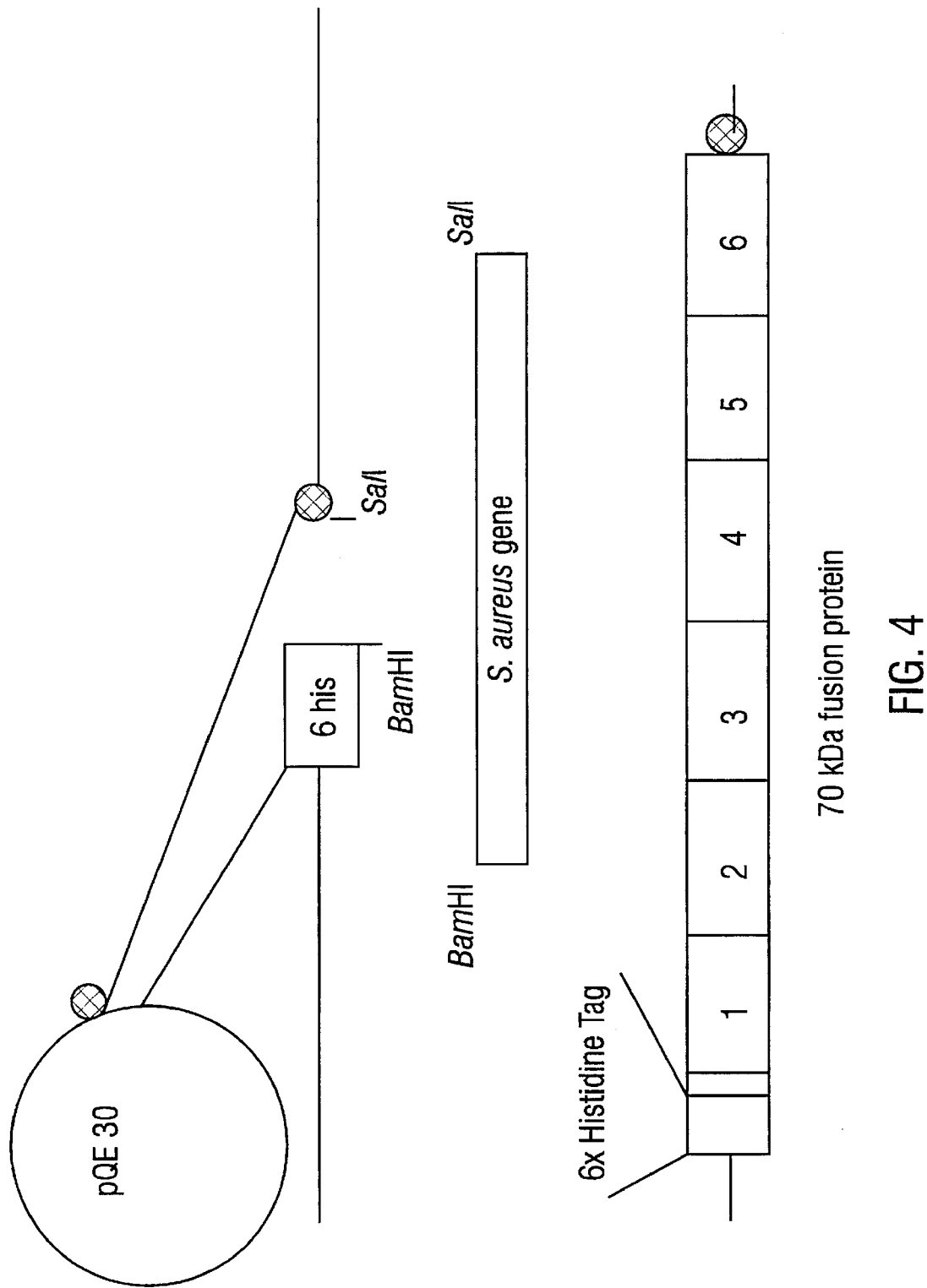
FIG. 4 illustrates the MHC II-antigen like staphylococcal protein gene introduced into the pQE expression vector and used to express the recombinant protein.

It will be readily apparent to one skilled in the art that various substitutions and modifications may be made to the invention disclosed herein without departing from the scope and spirit of the invention.

As used herein, the term "extracellular matrix proteins" refers to four general families of macromolecules—collagens, structural glycoproteins, proteoglycans and elastins—that provide support and modulate cellular behavior.

The term "MHC Class II antigens" or "MHC II antigens" as used herein refers to cell-surface molecules that are responsible for rapid graft rejections and are required for antigen presentation to T-cells.

As used herein, the term "in vivo vaccine" refers to immunization of animals with proteins so as to elicit a humoral and cellular response that protects against later exposure to the pathogen.

As used herein, fie term "autoimmune diseases" refers to an abnormal response against self-antigens.

Staphylococcus aureus can bind a number of different extracellular matrix proteins. Recent studies have shown that one particular Staphylococcus protein has the capacity of binding several different matrix proteins. This staphylococcal protein has been found to occur in two different forms, a 68 kD form and a 70 kD form. The gene encoding this staphylococcal protein has been cloned and sequenced. Comparison with existing data bases (Gen Bank EMBL) show that this staphylococcal protein has a high degree of homology with eukaryotic MHC Class II antigens.

Further analyses of the binding specificities of this protein reveal that it functionally resembles an MHC II antigen in that it binds synthetic peptides. Thus, in addition to mediating bacterial adhesion to extracellular matrix proteins, one may expect this protein to play a role in staphylococcal infections by suppressing the immune system of the host. Therefore, this protein, or derivatives thereof, are useful as important vaccine components for protection against staphylococcal infections.

In one embodiment of the present invention there is a nucleotide sequence (SEQ ID NO:1) that codes for a gene that is transcribed and translated into an MHC II-antigen like staphylococcal protein. There is further provided the amino acid sequence of the MHC II-antigen like staphylococcal protein having the formula of SEQ ID NO:2.

In another embodiment of the present invention, an in vivo vaccine against staphylococcal infections is provided. This vaccine comprises an MHC II antigen protein analog which elicits a humoral and cellular response protects against later exposure to the antigen.

Moreover, a method for using the in vivo vaccine is provided. The method involves the steps of expression of the MHC II antigen analog protein in a recombinant system, purification to homogeneity, and immunization using the protein in a pharmaceutically acceptable dispensing agent. Different routes of immunization may be used and various adjuvants may be added so that optimal dosage can be achieved. In order to obtain sufficient levels of antigen in the body, multiple injections will be used. Additionally, passive immunization of affected individuals is used if needed.

The following examples are offered by way of illustration and are not intended to limit the invention in any manner.

EXAMPLE 1

Bacterial strains and plasmids

The S. aureus clinical isolates were provided by the Department of Orthopedics, Bowman Gray School of Medicine, Winston-Salem, N.C., and the Clinical Pathology Laboratory, School of Medicine, University of Alabama at Birmingham (Homonylo-McGavin, M., et.al., Infect. Immun. 61:2479–2485 (1993)).

E-coli DH-5α (Hanahan, D., J. Mol. Biol. 166:557–580 (1983)) and M15 (Henco, K., The QIAexpressionist, DIAGEN GmbH, Düsseldorf (1991)) were used as bacterial hosts. The plasmid vectors were BluescriptSK(+) (Stratagene Cloning Systems, La Jolla, Calif.) and pQE30

(Henco, K., *The QIAexpressionist*, DIAGEN GmbH, Düsseldorf (1991)). Chromosomal DNA was prepared from *S. aureus* FDA 574 as previously described (Marmur, J., *J. Mol. Biol.* 3:208–218 (1961)).

EXAMPLE 2

Media and growth conditions

*E. coli* clones of the strain DH-5α were grown in Luria broth (LB), supplemented with ampicillin (100 μg/ml). The *E. coli* clone pQE20 (fusion of the pQE30 with the gene of the broad spectrum adhesin), was grown in LB supplemented with ampicillin at a concentration of 100 μg/ml and kanamycin at a concentration of 25 μg/ml. The clone was induced for expression of the recombinant gene with 1 mM isoprophyl β-thiogalactoside (IPTG) for 4 hours.

*S. aureus* FDA 574 was grown in LB over night at 37° C. for the subsequent purification of the broad spectrum adhesin. The *S. aureus* clinical isolates were grown 15 hours in either Tryptic Soy Broth or LB.

EXAMPLE 3

Solubilization of *S. aureus* proteins

Overnight cultures of *S. aureus* cells were harvested by centrifugation, boiled in PBS 2% sodium dodecylsulfate (SDS) and 5% 2-mercaptoethanol for 3 minutes and loaded onto a SDS-polyacrylamide gel (PAGE) for electrophoresis.

EXAMPLE 4

Lithium chloride extraction of the extracellular matrix protein with broad specificity Overnight grown bacterial cultures of *S. aureus* FDA 574 were harvested by centrifugation (3,600×g, 20 min) and resuspended in ⅟₁₀ volume of 1M LiCl (pH 6.0). The cell suspension was incubated at 45° C. for 2 hours with gentle agitation. Subsequently, the cells were removed by centrifugation (3,600×g 30 min), and the supernatant containing the solubilized protein was collected. The protein was precipitated from the LiCl extracts by addition of ammonium sulfate to a final concentration of 60% (wt/vol), followed by gentle stirring overnight at 4° C. The precipitated protein was recovered by centrifugation (15000×g, 30 min), and the pellet was resuspended in a minimal volume of 10 mM Tris-HCl, pH 7.5.

EXAMPLE 5

Iodination of ligands

Iodination of ligands were conducted by either the chloramine-T method of Hunter (Hunter, H. and K. M. Wier, *Handbook of Experimental Immunology*, p. 14.1–14.40 (1968)) or the lactoperoxidase method (Morrison, M., and G. S. Bayse, *Biochemistry* 9:2995–3000 (1970)) using Enzymobeads (Bio-Rad Laboratories, Hercules, Calif.).

EXAMPLE 6

Detection of the broad spectrum component by Western blotting

Proteins were fractionated by SDS-PAGE using a gradient gel of 3 to 15% acrylamide or a 10% acrylamide SDS-PAGE gel and the buffer system of Laemmli (*Nature* 227:680–685 (1970)). The proteins were transferred to Immobilon P™ (Millipore, Bedford, Mass.) membranes with the Bio-Rad Trans Blot™ apparatus and the transfer buffer of Towbin et al. (Towbin, H., et al., *PNAS* 76:4350–54 (1979)). Additional protein binding sites on the membranes were blocked by incubation for 2 hours to 15 hours in phosphobuffered saline (PBS) containing 3% (wt/vol) bovine serum albumin (BSA). Membranes were then incubated overnight at 4° C. with gentle agitation in a solution containing $5 \times 10^5$–$6 \times 10^7$ cpm of $^{125}$I-labeled ligand or in PBS containing 0.1% BSA. Subsequently, the membranes were washed extensively with PBS containing 0.1% Tween™, air dried, and exposed to Fuji RX-100 X-ray film for anywhere from 12 to 36 hours.

EXAMPLE 6

Amino acid sequencing

LiCl purified protein from *S. aureus* FDA 574 was blotted to Immobilon P™ and N-terminal sequenced in the Core Facility at Baylor College of Medicine, Houston, Tex. Peptide fragments derived from the broad spectrum adhesin of *S. aureus* strain Newman were obtained by cleaving the protein with trypsin and purified on FPLC. The N-terminal sequence of the purified peptides were sequenced according to the method in the University of Alabama at Birmingham Cancer Center Protein Analysis and Peptide Synthesis Core Facility.

EXAMPLE 7

Cloning and DNA sequencing

Polyclonal antibodies raised in rabbits against purified *S. aureus* (FDA 574) broad spectrum adhesin were used to screen a lambda-gt 11 gene library (CLONTECH Laboratories, Inc., Palo Alto, Calif.) of the *S. aureus* FDA 574 strain. One clone with a 5.7 kb insert was detected and was subsequently used as a template for Polymerase Chain Reaction (PCR) analysis using a primer pair with sequences derived from the *S. aureus* 25923 OMP-70 sequence (SwissProt Database #P21223). This OMP-70 sequence was not the complete sequence and contained only the four hundred first nucleotides of a gene coding for a putative 70 kD outer surface protein, however, this sequence coded for nearly the same amino acids obtained from peptide sequences derived from the broad spectrum adhesin implicating that the two proteins were very closely related. A 400 nucleotide fragment obtained from the PCR reaction was cloned into Bluescript. DNA was sequenced using the Sanger method (Sanger, F. et.al., *PNAS* 74:5463–5467 (1978)) with the Sequenase™ DNA sequencing kit (U.S. Biochemical, Cleveland, Ohio) and the thermocycling sequencing method using Circum Vent Thermal Cycle Dideoxy DNA Sequencing Kit (New England BioLabs, Beverly, Mass.). The sequence coding for the 10 amino acids after the putative signal sequence corresponded exactly to the amino acid sequence obtained from the N-terminal sequence of the LiCl purified protein of *S. aureus* FDA 574.

Additional lambda-gt 11 clones were isolated by using a random prime labeled gene fragment from the cloned 400 bp fragment as a probe in a plaque hybridization assay. The plaques were detected with the ECL system by Amersham. DNA from the lambda plaques were cloned into the Bluescript vector and sequenced with the above mentioned DNA sequencing methods. Various oligonucleotides corresponding to sequences from the Bluescript clones were used as DNA sequencing primers.

The construction of the recombinant plasmid pQE20, containing the gene for the broad spectrum adhesin fused to the 6 histidine residues tag of pQE30, was obtained by inserting a 2 kb DNA fragment amplified from chromosomal *S. aureus* FDA 574 DNA into the cleavage sites Bam HI/Sal I of plasmid pQE 30. The primers ZPCR6 5'CGGGATC-CGCAGCTAAGCAAATAGATA (SEQ ID NO:24) 3' and ZPCR9 5'GCGTCGACGCGGCAAATCACTTCAAGT (SEQ ID NO:25) were used in the PCR reaction. The primers contain the restriction cleavage sites Bam HI and Sal I respectively (underlined).

EXAMPLE 8

Evaluation of the MHC II-antigen protein analog gene from *Staphylococcus aureus* as a virulence factor In order to evaluate the importance of the broad spectrum adhesin as a virulence factor in staphylococcal-induced diseases such as septic arthritis osteomyelitis and endocarditis, isogenic mutants are constructed and compared with its parent strains in animals models. Histopathological as well as bacteriological analysis is performed.

In the first class of mutants, the gene for the broad spectrum adhesin is inactivated in clinical isolates. Then the mutant as well as the parent strain is tested in an animal model for the disease. In the second type of mutant, the intact gene is introduced into an *S. aureus* strain that lacks the gene and this transformed strain is compared to its parent strain in the appropriate animal model.

Methods: For the first class of mutations, allele replacement shuttle vectors, containing a temperature sensitive origin of replication, is constructed and introduced in *E. coli*. In these constructions, the gene for the broad spectrum adhesin is insertionally inactivated by a resistant marker. The shuttle vector is then introduced into the *S. aureus* strain of interest where the insertionally inactivated gene can recombine into the *S. aureus* chromosome after raising the temperature of the growth medium. A detailed description of this methodology is described in Patti, J., et al., *Infection and Immunity*, 62:152–61 (1994).

EXAMPLE 9

Evaluation of inactivated versions of the MHC II-antigen protein analog gene from *Staphylococcus aureus* as a potential vaccine The animal models in Example 8 are used for the evaluation of inactivated (deleted) versions of the MHC II analog. The intact MHC II analog as well as various deletions of MHC II and its peptides are used in vaccination trials in the animal models.

Methods: Different parts of the gene are expressed and the gene products are tested for their binding capacity to the different extracellular matrix proteins. Synthetic peptides mimicking the 30 amino acid subsegments of the MHC II molecules are also used. For example, the minimal stretch of amino acids in the broad spectrum adhesin for binding to the various extracellular proteins is characterized, and the binding capacity of the synthetic peptides are compared to it. Further, modifications of the synthetic peptides are made by conventional means and tested for higher binding capacity. All these different constructions are then used to immunize animals, and the antibodies are tested for inhibitory capacity of the binding of *S. aureus* to various extracellular matrix proteins. The animals are then challenged with the clinical *S. aureus* isolates and evaluated for the incidence of infection by histopathological examination and bacteriological analysis of the tissues.

EXAMPLE 10

The ability of the MHC II analog to interfere with MHC II dependent antigen

The MHC II analog is tested in microtiter well assays with macrophages and CD4 T-helper cells. The peptide presenting macrophages/monocytes with their MHC II molecules are "fed" with peptide and mixed with T-helper cells as well as analog. The proliferation of the CD4 T-helper cells is stopped when the analog interferes with the peptide presentation. Macropages fed with the Vn peptide activates the T-helper cells. A determination of whether the analog can interfere in this cell assay system is made. Cell assays of this type are easily visualized under a microscope. Studies of the secretion of cytokines from the T-cells are also conducted using the cell assay. The assay is useful in this context because T-cells produce cytokines when they are stimulated. Secretion levels can be measured by using antibodies directed against the cytokines in microtiter well assays.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will appreciate readily that the present invention is will adapted to carry out the objects and attain the ends and advantages mentioned as well as those inherent therein. The sequences, methods, procedures and techniques described herein are presently representative of the preferred embodiments and are intended to be exemplary and ar not intended as limitations of the scope. Changes therein and other uses will occur to those skilled in the art which are encompassed within the spirit of the invention or defined by the scope of the appended claims.

---

We claim:

1. A DNA segment comprising an isolated gene encoding a *Staphylococcus aureus* broad spectrum adhesin that has a molecular weight of about 70 kDa as determined by SDS gel electrophoresis, said adhesin capable of binding fibronectin or vitronectin wherein said adhesin comprises a MHC II mimicking unit of about 30 amino acids.

2. The DNA of SEQ ID NO:1 or fragment thereof that encodes a protein or peptide that is capable of binding fibronectin or vitronectin or that comprises a MHC II mimicking unit of about 30 amino acids.

3. The DNA of claim 2 that encodes a protein or peptide that encompasses a MHC II mimicking unit.

4. The DNA of claim 2 that encodes a protein or peptide that binds to fibronectin or vitronectin.

5. The DNA of claim 2, comprising a gene that encodes a protein of about 689 amino acids in length.

6. The DNA of claim 2, positioned under the control of a promoter.

7. A recombinant vector comprising the DNA segment of claim 2.

8. The vector of claim 7, further defined as pQE20.

9. A recombinant host cell transformed with the vector of claim 7.

10. The recombinant host cell of claim 9, further defined as a bacterial host cell.

11. The recombinant host cell of claim 10, wherein the bacterial host cell is *E. coli*.

12. The recombinant host cell of claim 9, that expresses the polypeptide encoded by the DNA of claim 2.

13. A fragment of the DNA sequence of SEQ ID NO:1 that hybridizes to the DNA sequence of claim 2.

14. The DNA of claim 13, wherein the segment is SEQ ID NO:1.

15. The DNA of claim 13, that is the complement of SEQ ID NO:1.

16. The DNA of claim 13, wherein the segment comprises residues 71 to 2134 of FIG. 2.

17. The DNA of claim 13, which encodes an amino acid sequence set forth by any one of SEQ ID NOS:2, 3, 4, 5, 6, 7, or 8.

18. An isolated nucleic acid composition comprising the DNA sequence of SEQ ID NO:1 or the complement thereof in a suitable buffer.

19. A composition comprising a protein or polypeptide encoded by the DNA of claim 2 and a pharmaceutically acceptable excipient.

20. The composition of claim 19, comprising a peptide that consists of the amino sequence of SEQ ID NO:3, SEQ ID NO:4, SEQ ID NO:5, SEQ ID NO:6, SEQ ID NO:7 or SEQ ID NO:8.

21. A method of inducing an immune response in an animal comprising administering to an animal an immunogenic composition comprising the composition of claim 19 and a pharmaceutically acceptable dispensing agent.

22. A method of making a MHC II-antigen protein analog comprising the steps of inserting the DNA of SEQ ID NO:1 in a suitable expression vector and culturing a host cell transformed with said vector under conditions to produce said MHC II-antigen protein analog.

23. A method of inducing an immune response to *Staphylococcus aureus* comprising the steps of administering to an individual suspected of being susceptible to or having a staphylococcal infection a pharmaceutically acceptable composition in accordance with claim 19.

* * * * *

UNITED STATES PATENT AND TRADEMARK OFFICE
CERTIFICATE OF CORRECTION

PATENT NO. : 5,648,240
DATED : July 15, 1997
INVENTOR(S) : Hook et al.

It is certified that error appears in the above-indentified patent and that said Letters Patent is hereby corrected as shown below:

```
Column 1, line 23, after 'increase', delete --of--.
Column 1, line 66, after 'Infect', insert --,--.
Column 4, line 7, delete "fie", and insert --the-- therefor.
Column 5, line 1, after 'GmbH', delete --D--.
Column 5, line 2, delete "üsseldorf", and insert --Düsseldorf--
therefor.
Column 7, line 4 and 5, delete "5'CGGGATC-
CGCAGCTAAGCAAATAGATA", and insert therefor --5'CGGGATC-
CGCAGCTAAGCAAATAGATA-- therefor.
Column 7, line 5, delete "3'" and insert --3'-- before (SEQ.
Column 7, line 6, delete "5'GCGTCGACGCGGCAAATCACTTCAAGT", and
insert -- 5'GCGTCGACGCGGCAAATCACTTCAAGT-- therefor.
Column 7, line 42, delete "H-" and insert --II--- therefor.
Column 8, line 44, delete "will" and insert --well-- therefor.
Column 8, line 49, delete "ar" and insert --are-- therefor.
```

Signed and Sealed this

Twenty-eighth Day of October, 1997

Attest:

BRUCE LEHMAN

Attesting Officer

Commissioner of Patents and Trademarks